United States Patent [19]

Nakatani et al.

[11] 4,066,707

[45] Jan. 3, 1978

[54] METHOD FOR MANUFACTURE OF DIPHENOLS AND MONOALKYL ETHERS OF DIPHENOLS

[75] Inventors: Kiyoshi Nakatani, Tokyo; Juichi Imamura, Chofu; Toshiyuki Ichikawa, Tokyo; Kouichi Takeuchi, Yokohama; Kenji Kotaka, Tokyo, all of Japan

[73] Assignees: Agency of Industrial Science & Technology; Mitsui Toatsu Chemicals, Incorporated, both of Tokyo, Japan

[21] Appl. No.: 717,534

[22] Filed: Aug. 25, 1976

[30] Foreign Application Priority Data

Aug. 28, 1975    Japan ............................... 50-104451

[51] Int. Cl.² ............................................ C07C 37/00
[52] U.S. Cl. ............................. 260/613 R; 260/613 D; 260/621 G; 260/625

[58] Field of Search .......... 260/621 G, 502 R, 613 D, 260/625, 613 R

[56] References Cited

U.S. PATENT DOCUMENTS

| | | | |
|---|---|---|---|
| 3,376,351 | 4/1968 | Amedjian et al. ............... | 260/613 D |
| 3,514,490 | 5/1970 | Marlard ........................... | 260/621 G |
| 3,849,502 | 11/1974 | Bourdin et al. ................. | 260/613 D |
| 3,950,437 | 4/1976 | Imamura et al. ................ | 260/621 G |

*Primary Examiner*—Bernard Helfin
*Attorney, Agent, or Firm*—Oblon, Fisher, Spivak, McClelland & Maier

[57] ABSTRACT

Diphenols, alkyl ethers and aryl ethers of diphenols are produced by subjecting phenols, alkyl ethers and aryl ethers of phenols to oxidation with an organic per-acid in the presence of at least one member selected from the group consisting of acetyl acetone and acetonyl acetone as the catalyst.

6 Claims, No Drawings

METHOD FOR MANUFACTURE OF DIPHENOLS AND MONOALKYL ETHERS OF DIPHENOLS

BACKGROUND OF THE INVENTION

This invention relates to a method for manufacturing diphenols and monoalkyl ethers and monoaryl ethers of diphenols having the hydrogen atom of one hydroxyl group thereof substituted with an alkyl group or aryl group by subjecting to oxidation with an organic per-acid corresponding phenols and alkyl ethers and aryl ethers of phenols having the hydrogen atom of the hydroxyl group thereof substituted with an alkyl group or aryl group.

Pyrocatechol and hydroquinone are highly useful compounds as antioxidants for various materials, polymerization inhibitors for monomers, medical and pharmaceutical stocks, spices, dyestuffs, intermediates for rubber stocks and photographic materials. Heretofore, pyrocatechol has been produced by a method which extracts the compound from the dry distillate of coal or a method which obtains the compound by hydrolyzing ortho-chlorophenol, for example. Hydroquinone has been produced by a method which obtains the compound by oxidizing aniline with manganese dioxide and sulfuric acid. The issues concerning the preservation of natural resources and the prevention of environmental pollution which have been brought to the public attention in the past years are encouraging a shift from existing unsafe processes to safe ones. There have been proposed many methods obtain pyrocatechol and hydroquinone by oxidizing phenols with hydrogen peroxide or with a per-acid. Methods which involve the oxidation of phenols with peracids have been disclosed by French Pat. No. 1,479,354 and by Ogata et al's article in the "Kogyo Kagaku Zasshi", Vol. 73, page 1849, published in 1970 by the Japan Chemical Society. And methods which involve the oxidation with hydrogen peroxide have been suggested by German Pat. No. 2,064,47, Japanese Patent Disclosure No. 34325/1972 and Japanese Patent Disclosure No. 30330/1974, for example.

The method which involves use of hydrogen peroxide as disclosed by German Pat. No. 2,064,497 is dangerous since the hydrogen peroxide to be used is required to have a high concentration of not less than 60 percent. The methods which permit use of a low-concentration aqueous solution of hydrogen peroxide require use of a metal salt (Japanese Patent Disclosure No. 28435/1973) and an organic metal chelate (Japanese Patent Disclosure No. 30330/1974) respectively as the catalyst. In the case of the method which involves use of the metal salt, said metal salt persists in the water phase during the extraction of the reaction product with an organic solvent and consequently passes into the waste water, entailing the possibility of water pollution. Thus, the process cannot be carried out in a closed system unless there is incorporated an extra facility for the removal of such unwanted metal. Otherwise, the water phase containing the metal salt in a dilute sate is concentrated to the extent of enabling the metal salt to be recovered and recycled in the process. This operation, therefore, calls for large equipment cost and heavy energy consumption. In the case of the method which involves use of the organic metal chelate compound as the catalyst, an organic solvent is used to extract the product aimed at from the reaction mixture. In the course of said extraction, the organic metal chelate compound dissolves into the organic phase and, consequently, in the subsequent course of distillation effected for separating the product from said organic phase, accelerates conversion of the product into tar. Moreover, the utility ratio of hydrogen peroxide falls short of 60 percent. Of the methods involving use of per-acids, the method disclosed by French Pat. No. 1,479,354 and the method proposed by Ogata et al in the Kogyo Kagaku Zasshi, Vol. 73, page 1849 synthesize the per-acids from aqueous solution of hydrogen peroxide and utilize the produced per-acids in situ. Thus, they are also dangerous since they involve use of an aqueous solution of not less than 60 percent of hydrogen peroxide. These methods, moreover, have the disadvantage that the yields are low, although use of such per-acids proves to be commercially advantageous in terms of the materials of which the production system is made.

For the production of monoalkyl ethers or monoaryl ethers of diphenols by the oxidation of alkyl ethers or aryl ethers of phenols with per-acids, there has been proposed a method which effects the oxidation by use of an organic per-acid of high reactivity in the presence of a catalyst such as of boron trifluoride, for example (J. D. McClure: J. Org. Chem., 27, 627 (1962)). This method is still without advantage because of low yields despite use of an expensive per-acid, because of inferiority in terms of materials used in the reaction system, etc. As concerns the oxidation of alkyl phenols with per-acids, no research directed to the synthesis of alkyl pyrocatechol has been brought to knowledge in the art.

One of the inventors of the present invention made a study in search of catalysts effective in oxidizing phenols with per-acids and arrived at the discovery that per-acid stabilizers, nitrogen group- or hydroxyl group-containing polycarboxylic acids possessed of an ability to chelate heavy metal ions, salts of said acids and acidic low esters of phosphoric acid and pyrophosphoric acid exhibit excellent catalytic activity (Japanese Patent Disclosure No. 86334/1974, No. 102631/1974, No. 134636/1974, No. 47934/1975, No. 49237/1975 and No. 76031/1975).

The catalysts to be used in the methods disclosed in said Japanese Patent disclosures exhibit inferior solubility in phenols or generally high boiling points, making it difficult to separate the catalysts from the formed products. Otherwise, they persist in the evaporators and consequently cause conversion of the formed products into tar. There is also a possibility that they decompose and give birth to various nitrogen-containing compounds, which possibly contaminate the end products and cause both internal and external contamination.

An object of the present invention is to provide a method for producing, without entailing the disadvantages attendant upon use of such known catalysts as described above, diphenols and monoalkyl ethers and monoaryl ethers of diphenols having the hydrogen atom of one hydroxyl group thereof substituted with an alkyl group or aryl group by subjecting to oxidation with an organic per acid the corresponding phenols and alkyl ethers and aryl ethers of phenols having the hydrogen atom of one hydroxyl group thereof substituted with an alkyl group or aryl group.

SUMMARY OF THE INVENTION

To accomplish the object described above according to this invention, there is provided a method which comprises oxidizing at least one member selected from the group consisting of phenols of the generic formula:

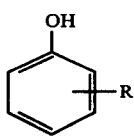

(wherein, R is selected from the group consisting of a hydrogen atom and alkyl groups having 1 to 12 carbon atoms) and alkyl ethers and aryl ethers of phenols of the generic formula:

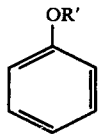

(wherein, R' is selected from the group consisting of alkyl or aryl groups having 1 to 12 carbon atoms) with an organic per-acid selected from the group consisting of performic acid, peracetic acid, perpropionic acid, perbutyric acid, perisobutyric acid, permonochloroacetic acid, pertrichloroacetic acid and perbenzoic acid in the presence of acetyl acetone and/or acetonyl acetone for thereby effecting introduction of hydroxyl group and producing the corresponding member of the group consisting of diphenols and alkyl ethers and aryl ethers having the hydrogen atom of one hydroxyl group thereof substituted with an alkyl or aryl group having 1 to 12 carbon atoms.

The other characteristics of the present invention will become apparent from the description to be given herein after.

DESCRIPTION OF THE PREFERRED EMBODIMENT

This invention relates to a method for the manufacture of diphenols and monoalkyl ethers and monoaryl ethers of diphenols having the hydrogen atom of one hydroxy group thereof substituted with an alkyl or aryl group, which method comprises oxidizing the corresponding phenols and alkyl ethers and aryl ethers of diphenols having the hydrogen atom of one hydroxyl group thereof substituted with an alkyl or aryl group with a per-acid in the presence of acetyl acetone and/or acetonyl acetone as the catalyst for thereby effecting introduction of a hydroxyl group and giving rise to the corresponding diphenols and alkyl ether and aryl ether derivatives thereof.

Use of acetyl acetone and acetonyl acetone in the oxidation of this kind has never been known in the art. These catalysts are organic compounds so easy to handle that they can readily be recovered from the reaction product by distillation and can be recycled in the process. The catalyst is required to be present at a proportion of 0.001 to 2 percent by weight, preferably 0.05 to 0.5 percent by weight, based on the compounds being used as the raw material.

The hydroxy groups which are introduced by this reaction of oxidation assume the ortho and para positions with respect to the hydroxy group, alkoxy group or aryloxy group of the compound as the raw material. When a phenol is used as the raw material, for example, the reaction products are pyrocatechol and hydroquinone.

The phenols which form a part of the compounds usable as the raw material in this invention are those represented by the generic formula:

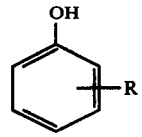

(wherein, R denotes a hydrogen atom or an alkyl (group). In the case of a phenol of this generic formula which has an alkyl group as the substituent R, the reaction aimed at proceeds without reference to the number of carbon atoms contained in the alkyl group. Only from the standpoint of practical convenience, the number of carbon atoms in the alkyl groups is limited to the range of 1 to 12. Examples of the phenol represented by this generic formula (I), therefore, include phenol, cresol, ethyl phenol, n-propyl phenol, isopropyl phenol, n-butyl phenol, secondary butyl phenol, isobutyl phenol, tertiary butyl phenol, n-pentyl phenol, isopentyl phenol, neopentyl phenol, secondary pentyl phenol, tertiary pentyl phenol, n-hexyl phenol, isohexyl phenol, (3-methylpentyl)-phenol, tertiary hexyl phenol, n-heptyl phenol, isoheptyl phenol, (3-methylhexyl)-phenol, tertiary heptyl phenol, n-octyl phenol, tertiary octyl phenol, (2-ethylhexyl)-phenol, isooctyl phenol, n-nonyl phenol, isononyl phenol, tertiary nonyl phenol, (3-methyloctyl)-phenol, (4-methyloctyl)-phenol, (2-isopropylhexyl) -phenol, n-decyl phenol, n-undecyl phenol and n-dodecyl phenol. As regards the alkyl phenol, those of ortho, meta and para forms are invariably usable as the raw material.

The alkyl ethers and aryl ethers of phenols which form the remaining part of the compounds usable as the raw material are those represented by the generic formula:

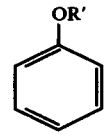

(wherein, R' denotes an alkyl or aryl group). The reaction involving the use of these phenol derivatives proceeds without reference to the number of carbon atoms of the substituent R'. Only from the standpoint of practical convenience, the number of carbon atoms of said substituent is limited to the range of from 1 to 12. Examples of the alkyl ether of phenol usable in this invention, therefore, include anisole, phenetole, n-propoxy benzene, isopropoxy benzene, n-butoxy benzene, secondary butoxy benzene, tertiary butoxy benzene, isobutoxy benzene, n-pentyl phenyl ether, isopentyl phenyl ether, neopentyl phenyl ether, secondary pentyl phenyl ether, tertiary pentyl phenyl ether, n-hexyl phenyl ether, isohexyl phenyl ether, (3-methyl-pentyl)-phenyl ether, tertiary hexyl phenyl ether, n-heptyl phenyl ether, isoheptyl phenyl ether, (3-methylhexyl)-phenyl ether, tertiary heptyl phenyl ether, n-octyl phenyl ether, tertiary octyl phenyl ether, (2-ethylhexyl)-phenyl ether, isooctyl phenyl ether, n-nonyl phenyl ether, isononyl phenyl ether, tertiary nonyl phenyl ether, (3-methyloctyl)

phenyl ether, (4-methyloctyl)-phenyl ether, (2-isopropylhexyl) -phenyl ether, n-decyl phenyl ether, n-undecyl phenyl ether and n-dodecyl phenyl ether. Examples of the aryl ether of phenol usable herein, therefore, include phenoxy benzene, benzyl oxy benzene, (ortho-, meta- and para-toluyl)-phenyl ether, phenetyl phenyl ether, (2,41 -dimethylphenoxy)-benzene, (2,6-dimethylphenoxy)-benzene, (2,4,6-trimethylphenoxy)-benzene, (4-tertiary butylphenoxy)-benzene, (2,6-dimethyl-4-tertiary butylphenoxy)-benzene, (2,6-dimethyl-4-isopropylphenoxy)-benzene, (2,4-diethylphenoxy)-benzene, (2,6-diethylphenoxy)-benzene, (2,4,6-triethylphenoxy)-benzene, (4-n-propylphenoxy)-benzene, (4-isopropylphenoxy)-benzene, (2,4-diisopropylphenoxy)-benzene and (2,6-diisopropylphenoxy)-benzene.

The organic per-acids which are usable in the reaction herein are aliphatic per-acids such as performic acid, peracetic acid, perpropionic acid, perbutyric acid, perisobutyric acid, permonochloroacetic acid and pertrichloroacetic acid and aromatic per-acids such as perbenzoic acid. The reaction can be carried out in a non-aqueous solution or an aqueous solution. With consideration for the material of the reaction system, the yield, the separation and purification of the final product, etc., however, it is more advantageous to carry out the reaction in a non-aqueous solution. As to the concentration of the per-acid to be used, there is a trend that the yield increases with the increasing concentration of said per-acid. From the standpoint of safety, however, it is desirable that the per-acid be used in the form of a solution containing said acid at a concentration of 10 to 40 percent in an organic solvent (such as ketone or ester) as is usual in the practice. If the proportion of the per-acid to the compound as the raw material is increased with a view to increasing the percent conversion, then the dioxy-benzene or monoether thereof which is formed, if any is formed at all, undergoes further oxidation to the extent of forming an oxide of higher degree, decomposition product or condensation product. It is, therefore, desirable that the proportion of the per-acid to the compound as the raw material be in the range of 0.3 to 0.01 mol, preferable 0.05 to 0.2 mol. The reaction hardly proceeds when this proportion is below the lower limit 0.01 mol. At a lower reaction temperature, the reaction velocity is too low to make the operation practicable. Neither is a higher reaction temperature desirable, for it not merely causes degradation in utility ratio of the per-acid due to decomposition but also entails oxidation or condensation of the final product to a higher degree. The suitable reaction temperature range, therefore, is from 30° to 150° C, preferably from 50° to 90° C. Since the heat of reaction is large, a short reaction time may possibly render difficult the removal of reaction heat on a commercial scale. A longer reaction time may result in quality degradation of the final product. The suitable range of reaction time, therefore, is from 10 to 200 minutes, preferably from 15 to 120 minutes.

As the catalyst, acetyl acetone (b.p. 137° C) and acetonyl acetone (b.p. 191.4° C) have no substantial difference in catalytic activity. The choice between the two catalyst must be made however, by taking into due consideration the convenience of recovery thereof at the end of the reaction, namely, the boiling point of the corresponding organic acid to be formed from the particular per-acid being used in the reaction.

As a specific method for the recovery of the used catalyst, where the reaction is carried out in a non-aqueous solution by using an acetone solution of peracetic acid as the oxidizing agent and acetyl acetone and/or acetonyl acetone as the catalyst, there may be adopted a procedure which comprises first distilling the reaction product for removing therefrom the acetone serving as the solvent for peracetic acid in conjunction with the acetic acid formed in consequence of the reaction and subsequently recovering acetyl acetone and/or acetonyl acetone by distillation. The recovered catalyst may be recycled in the process. In the case of a reaction wherein phenol is used as the raw material and acetonyl acetone as the catalyst, since the boiling point of this catalyst falls close to that of the unaltered phenol, the acetonyl acetone and the unaltered phenol can be recovered simultaneously by distillation and, in their unseparated state, recycled in the process.

In the case of a reaction which is carried out in an aqueous solution, there may be adopted a procedure which comprises first extracting the reaction product with an organic solvent and subsequently subjecting the extract to the same treatment as given in the case of the aforementioned reaction performed in a non-aqueous solution for thereby recovering the catalyst and recycling the recovered catalyst in the process. From the standpoint of the convenience of recovery and cyclic use, the organic solvent for use in this extraction is desired to be of a type having a boiling point different from that of the corresponding organic acid formed from the per-acid being used in the reaction, that of the solvent for said per-acid and that of the catalyst.

As is clear from the foregoing explanation, the final product, the solvent and the catalyst involved in the method of this invention can easily be separated by means of distillation and the reaction system can be closed completely. The method of this invention, therefore, is highly advantageous for the sake of prevention of environmental pollution and from the economic point of view as well.

Now, the present invention will be described more specifically with reference to working examples, which are cited solely for illustration and should not be considered limitations of the invention.

EXAMPLE 1

A reaction flask having an inner volume of 100 ml and provided with a thermometer, a stirrer, a reflux condenser and a dropping funnel was charged with 32.0 g (0.34 mol) of phenol and 0.0642 g (0.2 percent by weight based on said phenol) of acetyl acetone. To the contents of the flask, 7.6 g (0.034 mol) of an acetone solution of 34.0 percent by weight of peracetic acid was introduced introudced dropwise while under agitation at a temperature of 80° C over a period of 20 minutes. After the termination of said dropwise introduction of peracetic acid, the reaction system was agitated at the same temperature for an additional period of 42 minutes to bring the reaction to completion. Thereafter, the reaction mixture was analyzed for unaltered phenol and formed pyrocatechol and hydroquinone by gas chromatography. The results were 29.10 g, 1.66 g, and 1.09 g respectively. These values indicate the conversion of phenol to be 9.06 percent and the selectivity for dioxybenzene to be 73.5 percent relative to peracetic acid and 81.2 percent relative to phenol. From the reaction mixture, acetone, formed acetic acid and acetyl acetone were simultaneously recovered by distillation. When the recovered mixture was analyzed for acetyl acetone by means of gas chromatography, the acetyl acetone content was found be 0.0591 g. This value indicates the recovery ratio to be 92 percent.

EXAMPLE 2

The procedure of Example 1 was repeated, except that 11.8 g (0.034 mol) of an acetone solution of 30 percent by weight of perisobutyric acid was used in place of said acetone solution of peracetic acid and 0.0642 g of acetonyl acetone was used in place of acetyl acetone. In this case, the conversion of phenol was 8.71 percent and the selectivity for dioxybenzene was 89 percent relative to phenol and 78.7 percent relative to perisobutyric acid. The reaction mixture was distilled to separate acetone and isobutyric acid. Subsequently, acetonyl acetone was recovered in conjunction with phenol. Analysis of the recovered mixture showed the recovery ratio of acetonyl acetone to be 89 percent.

EXAMPLE 3

The procedure of Example 1 was repeated, except that 10.2 g (0.034 mol) of an acetone solution of 30 percent by weight of perpropionic acid was used in place of said acetone solution of peracetic acid and 0.0642 g of acetonyl acetone was used in place of acetyl acetone. The resultant reaction product was treated in the same manner as described in Example 2. The conversion of phenol was found to be 8.77 percent and the selectivity for dioxy-benzene to be 87.1 percent relative to phenol and 86.5 percent relative to perpropionic acid respectively. The recovery ratio of acetonyl acetone was 90 percent.

EXAMPLE 4

The procedure of Example 1 was repeated, except that 18.78 g (0.034 mol) of an acetone solution of 25 percent by weight of perbenzoic acid was used in place of said acetone solution of peracetic acid. The results showed the conversion of phenol to be 8.94 percent and the selectivity for dioxy-benzene to be 85.4 percent relative to phenol and 76.3 percent relative to perbenzoic acid respectively. By distillation, acetyl acetone was recovered in conjunction with acetone and acetic acid. The recovery ratio was found to be 87 percent.

EXAMPLE 5

The procedure of Example 1 was repeated, except that 0.0642 g of a 1 : 1 (gravitational ratio) mixture of acetyl acetone and acetonyl acetone was used in place of acetyl acetone. The results showed the conversion of phenol to be 9.00 percent and the selectivity for dioxy-benzene to be 82.1 percent relative to phenol and 73.7 percent relative to peracetic acid respectively. The recovery ratio of catalyst was found to be 91 percent.

EXAMPLE 6

The procedure of Example 1 was repeated, except that the amount of the peracetic acid solution was 3.8 g. The results showed the conversion ratio of phenol to be 4.61 percent and the selectivity for dioxy-benzene to be 85.3 percent relative to peracetic acid and 92 percent relative to phenol respectively.

EXAMPLE 7

A reaction flask having an inner volume of 200 ml and provided with a thermometer, a stirrer, a reflux condenser and a dropping funnel was charged with 54.05 g (0.50 mol) of para-cresol and 0.054 g of acetonyl acetone. While the resultant mixture was continuously stirred, 5.59 g (0.025 mol) of an acetone solution of 34.0 percent by weight of peracetic acid was introduced dropwise at a temperature of 80° C over a period of 20 minutes. After termination of the dropwise introduction of the peracetic acid solution, the reaction system was stirred at the same temperature for an additional period of 50 minutes to bring the reaction to completion. Thereafter, the reaction mixture was analyzed for unaltered para-cresol and formed 4-methyl-1,2-dihydroxybenzene by gas chromatography. The results showed the conversion of para-cresol to be 4.19 percent and the selectivity for 4-methyl-1,2-dihydroxybenzene to be 73.6 percent relative to peracetic acid and 88.4 percent relative to para-cresol respectively. From the reaction mixture, acetone, formed acetic acid and para-cresol were recovered by distillation. When the recovered mixture was analyzed for acetonyl acetone by gas chromatography, the recovery ratio of acetonyl acetone was found to be 88 percent.

COMPARISON EXAMPLE 1

The procedure of Example 7 was repeated, except that use of acetonyl acetone was omitted. The results showed the conversion of cresol to be 4.16 percent and the selectivity for 4-methyl-1,2-dihydroxybenzene to be 38 percent relative to peracetic acid and 51 percent relative to para-cresol respectively.

EXAMPLE 8

The procedure of Example 7 was repeated, except that 0.5 mol of ortho-cresol was used in place of para-cresol and the peracetic acid was used at a proportion of 0.05 mol and the reaction temperature was held at 50° C. Analysis of the reaction mixture by gas chromatograph showed the conversion of ortho-cresol to be 4.00 percent and the yields of 3-methyl-1,2-dihydroxybenzene and 2-methyl-1,4-dihydroxybenzene to be 35.6 mol percent and 33.9 mol percent respectively based on the consumed peracetic acid.

EXAMPLE 9

The procedure of Example 7 was repeated, except that 0.5 mol of meta-cresol was used in place of para-cresol and 0.05 mol of perpropionic acid was used in place of peracetic acid. The results showed the conversion of meta-cresol to be 3.8 percent and the yields of 3-methyl-1,2-dihydroxybenzene, 4-methyl-1,2-dihydroxybenzene and 3-methyl-1,4-dihydroxybenzene based on the consumed propionic acid to be 19.5 mol percent, 26.4 mol percent and 42.1 mol percent respectively.

EXAMPLE 10

The reaction apparatus used in Example 7 was charged with 75.1 g (0.5 mol) of para-tertiary-butyl phenol, 0.15 g of acetyl acetone and 15 ml of acetone as the solvent. While the contents of the apparatus were held at 60° C under continued agitation, 3.8 g (0.05 mol) of peracetic acid in the form of a 35 weight percent acetone solution was introduced dropwise over a period of 15 minutes. After termination of the dropwise introduction of said per-acid solution, the reaction mixture was held at the same temperature for an additional period of 60 minutes to bring the reaction to completion. The resultant reaction mixture was analyzed by gas chromatography. The results showed the conversion of para-tertiary butyl phenol to be 7.72 percent and the selectivity for para-tertiary-butyl catechol to be 79 percent relative to para-tertiary-butyl phenol.

COMPARISON EXAMPLE 2

The procedure of Example 10 was repeated, except that use of acetyl aetone was omitted. The results showed the conversion of para-tertiary-butyl phenol to be 5.1 percent and the selectivity for para-tertiary-butyl catechol to be 50 percent relative to para-tertiary-butyl phenol.

EXAMPLE 11

The procedure of Example 10 was repeated, except 103.2 g (0.5 mol) of para-tertiary-octyl phenol was used in place of para-tertiary-butyl phenol and 4.5 g (0.05 mol) of perpropionic acid in the form of a 25 weight percent acetone solution was used in place of said acetone solution of peracetic acid. The results showed the conversion of para-tertiary-octyl phenol to be 7.64 percent and the selectivity for para-tertiary-octyl catechol to be 65.6 percent relative to para-tertiary-octyl phenol.

EXAMPLE 12

The reaction apparatus used in Example 7 was charged with 54.0 g (0.5 mol) of anisole and 0.11 g of acetyl acetone.

While the contents of the apparatus were held at 80° C under agitation, 3.8 g (0.05 mol) of peracetic acid in the form of a 35 weight percent acetone solution was dropwise introduced thereto over a period of 20 minutes. Thereafter, the reaction mixture were held at the same temperature for an additional period of 100 minutes for completion of the reaction. The resultant reaction mixture was subjected to analysis by gas chromatography. The results showed the conversion of anisole to be 5.35 percent and the selectivity to be 56.5 percent for pyrocatechol-monomethyl ether and 33.2 percent for hydroquinone-monomethyl ether respectively relative to anisole. From the reaction mixture, acetone, acetic acid and anisole were distilled out. When the distillate was analyzed for acetyl acetone by gas chromatography, the recovery ratio of acetyl acetone was found to be 86 percent.

COMPARISON EXAMPLE 3

The procedure of Example 12 was repeated, except that use of acetyl acetone was omitted. The results shows the percent conversion of anisole to be 6.4 percent and the selectivity to be 39 percent for pyrocatechol-monomethyl ether and 17.8 percent for hydroquinone-monomethyl ether respectively relative to anisole.

EXAMPLE 13

The procedure of Example 12 was repeated, except that 61.1 g (0.5 mol) of phenetole was used in place of anisole. The results showed the percent conversion of phenetole to be 6.01 percent and the selectivity to be 53.2 percent for pyrocatechol-monoethyl ether and 25.3 percent for hydroquinone-monoethyl ether respectively relative to phenetole.

EXAMPLE 14

The procedure of Example 12 was repeated, except 85.1 g (0.5 mol) of diphenyl ether was used in place anisole and 17.35 g (0.05 mol) of an acetone solution of 30 weight percent of perisobutyric acid was used in place of said peracetic acid solution. The results showed the conversion of diphenyl ether to be 5.9 percent and the selectivity to be 49.3 percent for ortho-phenoxy phenol and 23.7 percent for paraphenoxy phenol respectively relative to diphenyl ether.

What is claimed is:

1. A method for the manufacture of at least one reaction product selected from the group consisting of diphenol and an ether of diphenol having the hydrogen atom of one hydroxy group thereof substituted with one member selected from the group consisting of alkyl and aryl groups of 1 to 12 carbon atoms, which method comprises subjecting at least one compound as the starting material selected from the group consisting of the compounds of the generic formula:

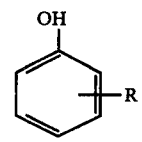
(I)

(wherein, R is selected from the group consisting of a hydrogen atom and alkyl groups having 1 to 12 carbon atoms) and the compounds of the generic formula:

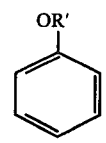
(II)

(wherein, R' is selected from the group consisting of alkyl and aryl groups having 1 to 12 carbon atoms) to oxidation at temperatures in the range of from 30° to 150° C for a period of from 10 to 200 minutes with at least one organic per-acid selected from the group consisting of performic acid, peracetic acid, perpropionic acid, perbutyric acid, perisobutyric acid, permonochloroacetic acid, pertrichloroacetic acid and perbenzoic acid in an amount corresponding to 0.01 to 0.3 mol based on the compound as the starting material in the presence of at least one catalyst selected from the group consisting of acetyl acetone and acetonyl acetone in an amount corresponding to 0.001 to 2% by weight based on the compound as the starting material.

2. A method as in claim 1, wherein the starting compound is

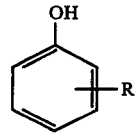

(wherein, R is one member selected from the group consisting of a hydrogen atom and alkyl groups having 1 to 12 carbon atoms) and the reaction product is a diphenol.

3. A method as in claim 2, wherein the starting compound is phenol and the reaction product consists of pyrocatechol and hydroquinone.

4. A method as in claim 3, wherein the catalyst is acetyl acetone.

5. A methods as in claim 3, wherein the catalyst is acetonyl acetone.

6. A method as in claim 1, wherein the starting compound is one member selected from the group of compounds represented by the generic formula:

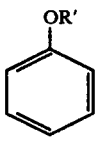

(wherein, R' is one member selected from the group consisting of alkyl groups and aryl groups having 1 to 12 carbon atoms) and the reaction product is one member selected from the group consisting of ethers of diphenols having the hydrogen atom of one hydroxy group thereof substituted with one member selected from the group consisting of alkyl and aryl groups of 1 to 12 carbon atoms.

* * * * *